United States Patent
Gobbi Frattini

(10) Patent No.: US 12,274,671 B2
(45) Date of Patent: **\*Apr. 15, 2025**

(54) STERILE FLEXIBLE PACKAGE WITH PRESSURE COMPENSATOR FOR THE DOSED RECONSTITUTION OF FLUID MEDICINAL OR NUTRITIONAL SUBSTANCES TO BE ADMINISTERED TO PATIENTS BY INFUSION OR INJECTION

(71) Applicant: ADIENNE S.A., Lugano (CH)

(72) Inventor: Paolo Giuseppe Gobbi Frattini, Sondalo (IT)

(73) Assignee: ADIENNE S.A., Caponago (IT)

( * ) Notice: Subject to any disclaimer, the term of this patent is extended or adjusted under 35 U.S.C. 154(b) by 576 days.

This patent is subject to a terminal disclaimer.

(21) Appl. No.: 17/498,464

(22) Filed: Oct. 11, 2021

(65) Prior Publication Data
US 2022/0133593 A1 May 5, 2022

Related U.S. Application Data

(63) Continuation of application No. 16/371,265, filed on Apr. 1, 2019, now Pat. No. 11,141,350.

(51) Int. Cl.
*A61J 1/20* (2006.01)
*A61J 1/10* (2006.01)
(Continued)

(52) U.S. Cl.
CPC .............. *A61J 1/2075* (2015.05); *A61J 1/10* (2013.01); *A61J 1/1475* (2013.01); *A61J 1/2062* (2015.05);
(Continued)

(58) Field of Classification Search
CPC .......... A61J 1/10; A61J 1/2089; A61J 1/2062; A61J 1/2058; A61J 1/2096; A61J 1/201;
(Continued)

(56) References Cited

U.S. PATENT DOCUMENTS 4,589,879 A * 5/1986 Pearson ................. A61J 1/2089
604/416
4,930,997 A * 6/1990 Bennett ................... A61M 1/84
604/319
(Continued)

FOREIGN PATENT DOCUMENTS

EP 0225861 A1 6/1987
EP 2399565 A1 * 12/2011 ............ A61J 1/2089
(Continued)

OTHER PUBLICATIONS

European Search Report for EP Application No. EP 19 16 5924, The Hague, Netherlands, dated Apr. 16, 2019, 5 pages.
(Continued)

*Primary Examiner* — Ariana Zimbouski
(74) *Attorney, Agent, or Firm* — STERNE, KESSLER, GOLDSTEIN & FOX P.L.L.C.

(57) ABSTRACT

The package comprises a sterile bag (3) filled with liquid diluent, a bottle (9) equipped with a pierceable cap (26) to contain a medicinal or nutritional substance and a tube (12) extending from the bag and ending with a coupling and perforation device (16) for the cap of the bottle. Said bag is housed in a flexible sterile sealed casing (1), while the bottle and the coupling and perforation device are accommodated in a second flexible sterile sealed casing (2). The tube (12) has a portion (13) between the first and second casing, housing a flow diverter (18) adjustable from a first position in which it impedes any communication between the bottle and the bag, to a second position in which it allows the bag to be put in communication with a sealed side opening (19) for a syringe (22), or a third position in which it allows the bottle to be connected with said side opening. To another side opening (41) of the flow diverter a flexible tube (42) with hydrophobic filter (43) is attached, terminating into one
(Continued)

and/or the other of said sterile sealed casings and serving as a pressure compensator(Fig. 1).

7 Claims, 6 Drawing Sheets

(51) Int. Cl.
*A61J 1/14* (2023.01)
*A61J 1/22* (2006.01)
*A61M 39/22* (2006.01)

(52) U.S. Cl.
CPC .......... *A61J 1/2082* (2015.05); *A61J 1/2089* (2013.01); *A61J 1/2096* (2013.01); *A61J 1/22* (2013.01); *A61M 39/22* (2013.01); *A61J 1/201* (2015.05); *A61J 1/2086* (2015.05); *A61M 2039/229* (2013.01); *A61M 2202/0208* (2013.01); *A61M 2202/0216* (2013.01); *A61M 2202/0482* (2013.01)

(58) Field of Classification Search
CPC ...... A61J 1/2075; A61J 1/1475; A61J 1/2082; A61J 1/1456; A61J 1/2048; A61M 2039/229; A61M 2202/0208; A61M 2202/0482; A61M 2202/0216; A61M 39/22; A61M 39/223
See application file for complete search history.

(56) References Cited

U.S. PATENT DOCUMENTS

| | | |
|---|---|---|
| 11,141,350 B2 | 10/2021 | Gobbi Frattini |
| 2007/0151984 A1* | 7/2007 | Baker .................. A61J 1/2089 222/129 |
| 2009/0254031 A1* | 10/2009 | Lee ....................... A61J 1/2096 604/83 |
| 2016/0000650 A1* | 1/2016 | Gobbi Frattini ... B65D 81/3216 604/408 |

FOREIGN PATENT DOCUMENTS

| | | |
|---|---|---|
| EP | 2962676 A1 | 1/2016 |
| EP | 3158987 A1 | 4/2017 |
| WO | WO-2011071952 A2 | 6/2011 |

OTHER PUBLICATIONS

Italian Search Report for IT application No. IT 201800004116, The Hague, Netherlands, dated Dec. 4, 2018, 7 pages.
Office Action for Indian Patent Application No. 201924011195, dated Jul. 19, 2022, Intellectual Property India, Mumbai, India, 6 pages.

* cited by examiner

STERILE FLEXIBLE PACKAGE WITH PRESSURE COMPENSATOR FOR THE DOSED RECONSTITUTION OF FLUID MEDICINAL OR NUTRITIONAL SUBSTANCES TO BE ADMINISTERED TO PATIENTS BY INFUSION OR INJECTION

CROSS-REFERENCE TO RELATED APPLICATIONS AND INCORPORATION BY REFERENCE

This application claims priority to U.S. patent application Ser. No. 16/371,265 filed on Apr. 1, 2019, which is incorporated by reference herein in its entirety for all purposes

BACKGROUND OF THE INVENTION

The present invention relates to a sterile flexible package for the dosed reconstitution of fluid medicinal or nutritional substances to be administered to patients by infusion or injection. The package is equipped with a pressure compensator to keep constant pressure applied on fluids during reconstitution.

Packages for intravenous infusions or instillations are known, which comprise a flexible bag in which a sterile chamber for containing a diluent is formed, and from which a flexible tube with an openable closure extends, equipped with a coupling and perforation device, through which a pharmaceutical or nutritional substance in powder, gel or other material is withdrawn from a bottle and delivered into the inner chamber of the bag, which substance, once mixed with the diluent, forms the medicament or nutrient to be supplied to the patient.

It is also known that sterility conditions must be preserved once the bottle is perforated in order to transfer the pharmaceutical or nutritional substance from the bottle into the bag.

While a loss in sterility is always dangerous, in the specific case of high-risk drugs this loss may lead to severe effects for both the patient and the medical and healthcare personnel responsible for the patient care. First, there is a the danger of an incorrect administration being performed, for example due to a premature or erroneous triggering of the drug reconstitution, or a risk of contamination of the medical and healthcare personnel or the patient themselves.

As a solution to this problem, packages where a single sterile flexible casing with airtight closure houses in separate chambers a flexible bag with liquid diluent and a bottle of medicinal or nutritional substance in powder, gel or other form equipped with a pierceable cap are known, in particular from EP 2962676 A1. Said casing also houses a mixing tube equipped with an openable closure extending from the bag and ending with a device allowing the coupling to the cap and the perforation of said cap. Initially, the bottle is inserted in the (still open) chamber of the casing in a coupling position to the coupling and perforation device and then, after said chamber has been hermetically sealed, may be manually maneuvered from outside of casing up to a perforating position of the cap through the coupling and perforation device itself.

Thus the flexible bag, the bottle with the pharmaceutical or nutritional substance and the coupling and perforation device for mixing the two products and reconstituting the desired drug or nutrient remain inside the sealed sterile casing, ensuring the implementation and maintenance of a completely sterile condition.

According to a variant described in EP 3158987 A1, the portion of flexible casing where the bottle is housed may be equipped with a connector with an openable and hermetically sealable cap, through which a mixture of a sterilizing gas and oxygen may flow into said portion of casing, thus ensuring an even higher sterility of the bottle and the entire package.

However, both solutions described above are limited to the reconstitution of a drug or nutrient comprising the total amount of pharmaceutical or nutritional substance contained in the bottle, and do not allow any dosing.

Such limitation makes both packages above completely useless when it is desired or even necessary to mix a dosed quantity of the medicinal or nutritional substance with the diluent contained in the bag in order to form a final drug or nutrient with a variable but precise dosing of substance.

On the other hand, a device for the dosed reconstitution of a drug or nutrient in a sterile bag with liquid diluent is known from EP 2399565 A1, in which a pharmaceutical or nutritional substance in powder, gel or other material is withdrawn in a dosed quantity from a bottle provided with a cap that can be hooked and perforated.

Said device comprises a 3-way flow diverter—like, by way of example, a stopcock—housed halfway a tube extending from the flexible bag and ending with a device for the coupling and perforation of the cap of the bottle.

When adjusted to a first position, the flow diverter impedes any communication between the bottle and the bag, while when moved to a second position it allows the bag to be put in communication with a side opening for a syringe or other plunger device, and when rotated up to a third position it allows the bottle and said side opening to be connected.

However, the solution described above does not ensure the sterility of the bottle when the cap is perforated through the coupling and perforation device of the tube extending from the bag, nor upon the coupling and removal of the syringe.

Lastly, it is known from the Italian patent application for utility model No. 202016000058207, filed on Jul. 6, 2016 in the name of the Applicant, a sterile flexible package comprising a sterile bag filled with liquid diluent, a bottle equipped with a pierceable cap to contain a medicinal or nutritional substance in powder, gel or other material, and a tube extending from the bag and provided with a device for the coupling and perforation of the cap of the bottle, where said bag is housed in a flexible, sterile and sealed casing, and said bottle and coupling and perforation device are accommodated in a second flexible, sterile and sealed casing. Said casings are separated and distanced, and said tube has a portion between the first and the second casing where an adjustable flow diverter is housed, which can be adjusted to a first position in which the bottle and the bag are prevented from being put in communication, a second position in which the bag communicates with an openable and hermetically sealable side opening for a syringe or other plunger device, or a third position in which the bottle is put in communication with said side opening.

By means of this package, using the syringe plunger first to withdraw the diluent from the bag and insert it in the bottle for mixing the diluent with the substance contained in the bottle and then to withdraw a dosed quantity of mixture from the bottle and insert it in the liquid diluent left inside the bag, the drug or nutrient can be reconstituted and administered in any dose desired and suitable for the therapeutic treatment of the patient.

The object of this invention is to improve said package in order to avoid possible issues caused by the pressure exerted by the syringe plunger first on the diluent withdrawn from the bag while being inserted into the bottle, and then on the dosed mixture withdrawn from the bottle while being inserted in the diluent left inside the bag.

SUMMARY OF THE INVENTION

According to the invention the object described above is achieved by equipping the package with a pressure compensator consisting of a small tube with hydrophobic filter connecting another side access of the flow diverter facing the one designed for the syringe to one or the other of said sterile and sealed casings.

This way the pressure exerted by pushing the syringe plunger on the liquid diluent first and then on the dosed mixture is released into one or the other of the casings, thus avoiding overpressure issues.

DESCRIPTION OF THE DRAWINGS

The features of this invention will become apparent from the following detailed description of an embodiment of the invention with reference to the appended drawings, provided purely by way of a non-limited example, in which.

DETAILED DESCRIPTION OF THE INVENTION

Figure 1:
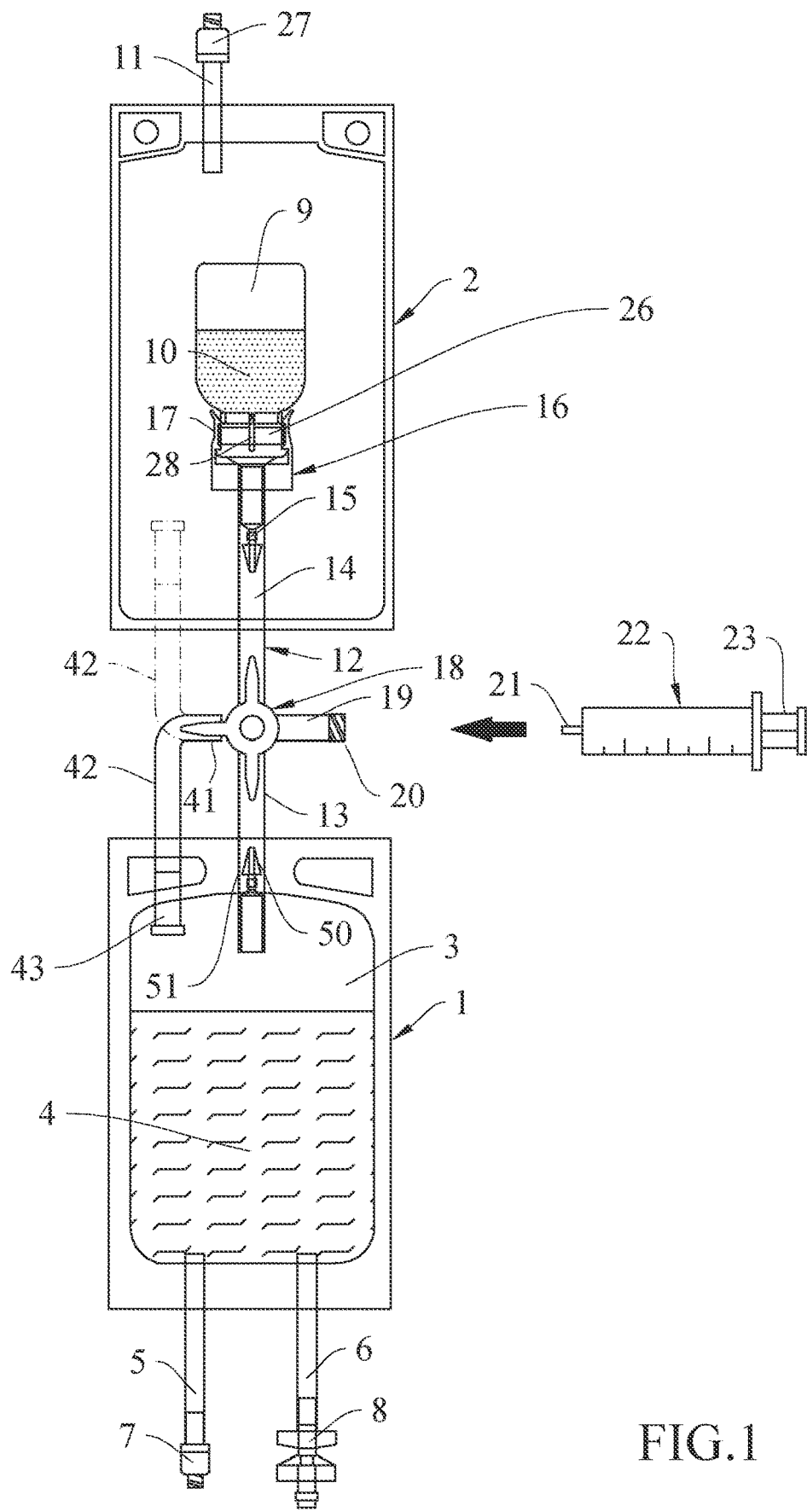
FIG. 1 illustrates the sterile and sealed package according to the invention and ready for use.

FIG. 1 shows two different casings 1 and 2, both sterile and sealed, that are aligned but distanced.

The lower or first casing 1 houses a flexible sterile bag 3 filled with a suitable liquid diluent and equipped with a flexible input tube 5 and a flexible output tube 6, both provided with caps 7 and 8.

The upper or second casing 2 accommodates a bottle 9 with a medicinal or nutritional substance 10 in powder, gel or other liquid material. The bottle is normally sealed with a cap 26. The cap 26 is of the type described in EP 2867132 A1 and can be opened by perforation with a syringe, luer or other piercing device, and is automatically airtight sealable once the perforation device is removed. The second casing 2 is also provided with a tube connector 11 with an airtight open/close cap 27 of the type described in EP 2867132 A1. The tube connector 11 can be used to deliver a mixture of ozone or other sterilizing gas and oxygen into the second casing 2.

The bag 3 and the bottle 9 are connected by a flexible tube 12, which consists of an initial section 51 extending from the bag 3 and out of the first casing 1 and including a frangible closure 50 of a known type, a middle portion 13 connecting casing 1 to casing 2, and a final portion 14 accommodated inside the second casing 2 and comprising a frangible closure 15 of a known type, and eventually ends with a coupling and perforation device 16 of the type described in EP 2962676 A1. Said coupling and perforation device is equipped with flaps 17 that can be coupled to the cap 26 of the bottle 9, and a perforation tip 28 to pierce the cap 26 of the bottle 9 after said cap has been coupled to the flaps 17 and a further axial movement has been made through pressure exerted on the outer walls of the second casing 2 in order to bring the bottle 9 closer to the bag 3, as described in further detail in EP 2962676 A1. For the sake of simplicity, the bottle 9 in FIG. 1 is already perforated and in a coupling position, but the frangible element 15 is still shown in a closed position.

The middle portion 13 of the flexible tube 12, located between the casings 1 and 2, comprises a flow diverter 18, by way of example a 4-way stopcock, in which a side opening 19 is closed with a cap 20 that can be perforated with the luer 21 (with or without needle) of a syringe 22 with plunger 23 and automatically sealed once the luer 21 is removed. Another side opening 41 of the flow diverter 18 is connected to a flexible tube 42 with hydrophobic filter 43 (FIG. 7) ending into one or the other of the casings 1 and 2, as shown in FIG. 1 with a continuous and dash-dotted line respectively. For the sake of simplicity and purely by way of example, FIGS. 2-6 illustrate only a tentative insertion of the tube 22 into the first casing 1 of the bag 3.

FIG. 1 shows the flow diverter 18 in a position where both the tube 12 and the side opening 19 are completely closed.

Figure 2:
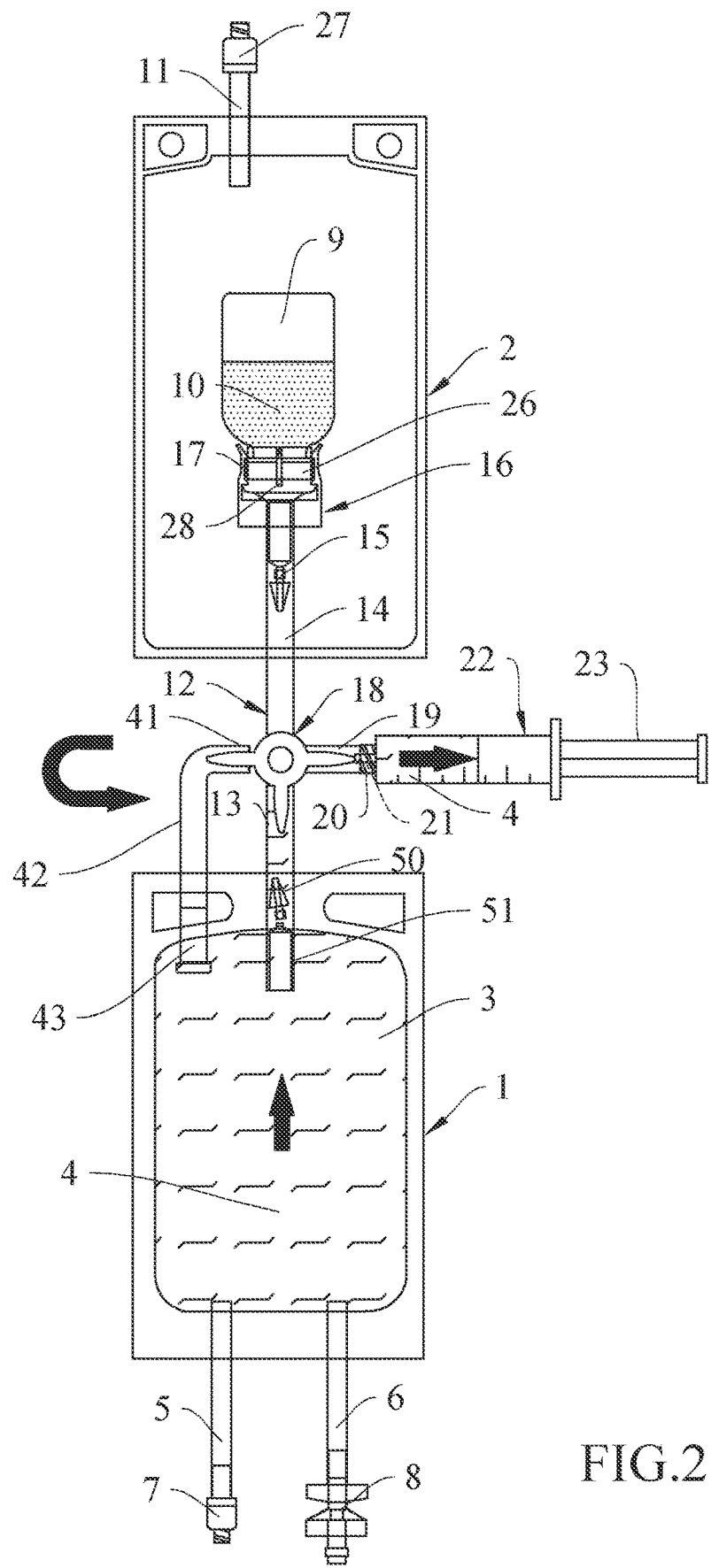
FIGS. 2-5 show the same package during the withdrawal, mixing and reconstitution procedures carried out by means of a syringe.

In order to trigger the reconstitution of the drug or nutrient inside the bag 3, the flow diverter 18 is to be adjusted to the position shown in FIG. 2, thus putting in communication the bag and the side opening 19, and then the luer 21 is inserted in the cap 20 in order to perforate it. Once the frangible closure 50 is broken, the syringe plunger 23, which is initially in a fully forward position, is pulled backwards to withdraw the desired quantity of diluent 4 from the bag 3.

Figure 3:
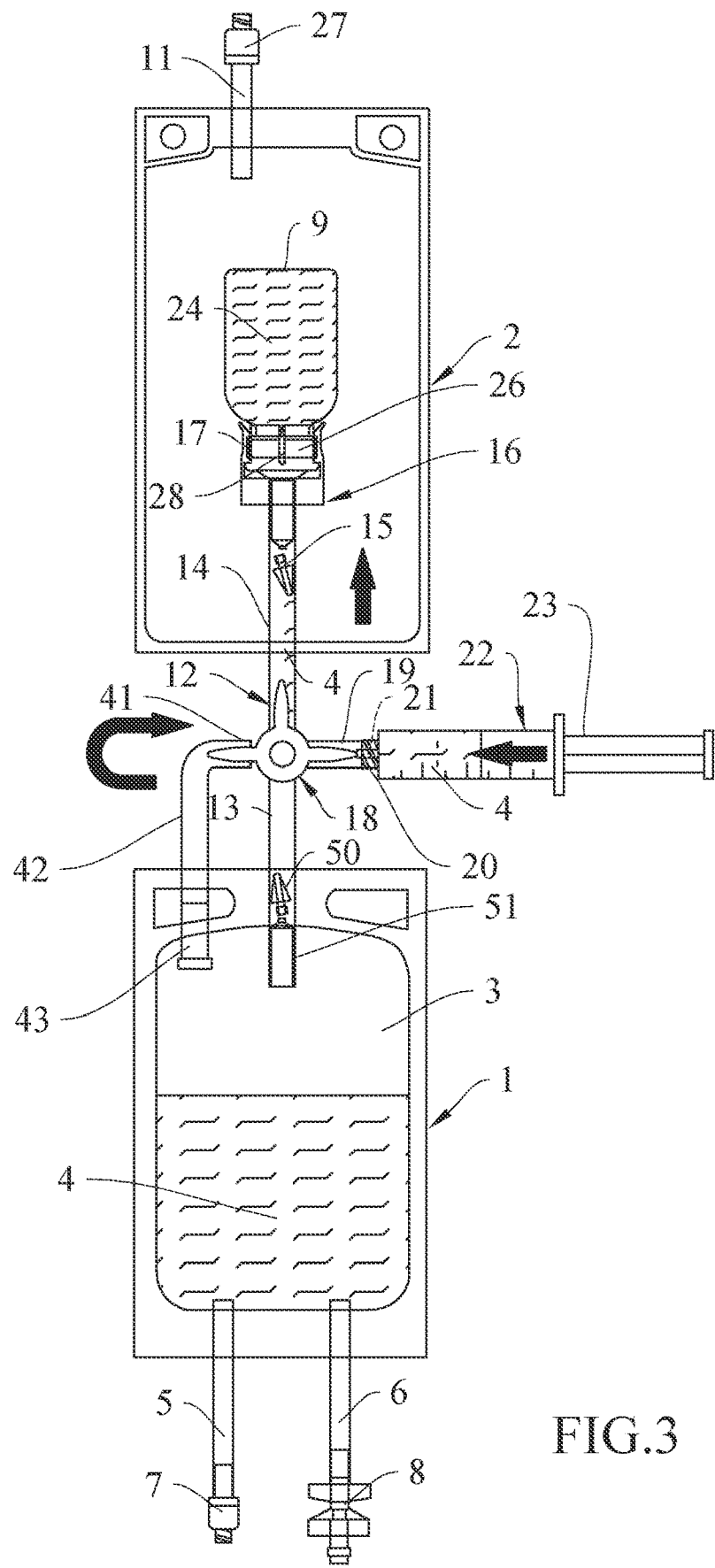

The flow diverter 18 is then rotated up to the position shown in FIG. 3, thus enabling communication between the portion of tube 14 and the side opening 19 with the luer 21 inserted. By breaking the frangible element 15 and pushing forwards the plunger 23 of the syringe 22, the amount of diluent which was previously drawn up can be transferred into the bottle 3, where said diluent is mixed with the medicinal or nutritional substance 10 contained therein and thus forming a mixture 24. At this stage, the flexible tube 42 with hydrophobic filter 43 serves as a pressure compensator terminating into a sterile casing, avoiding any possible toxic contamination for both the professional handling the package and the syringe and the patient receiving the fluid mixed substance.

Figure 4:
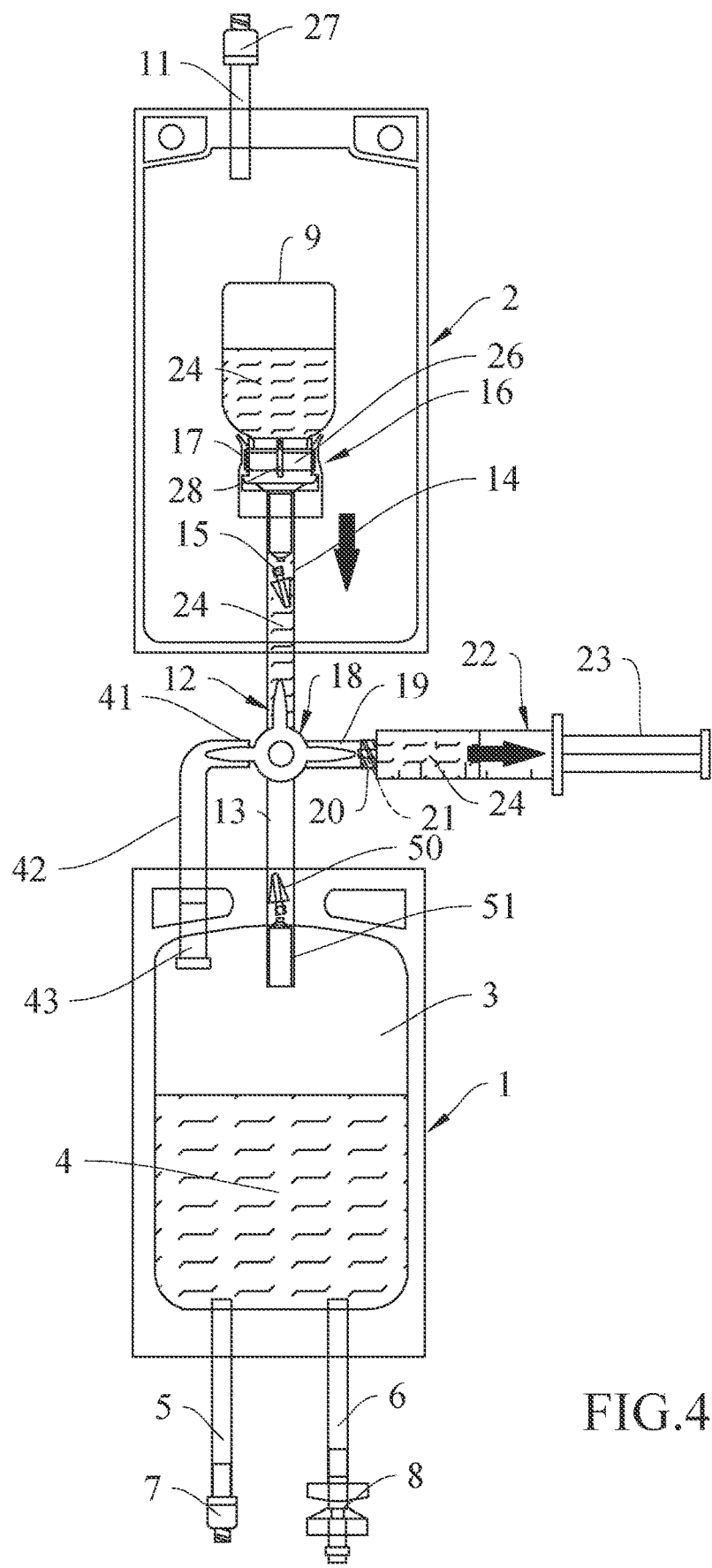
Figure 5:
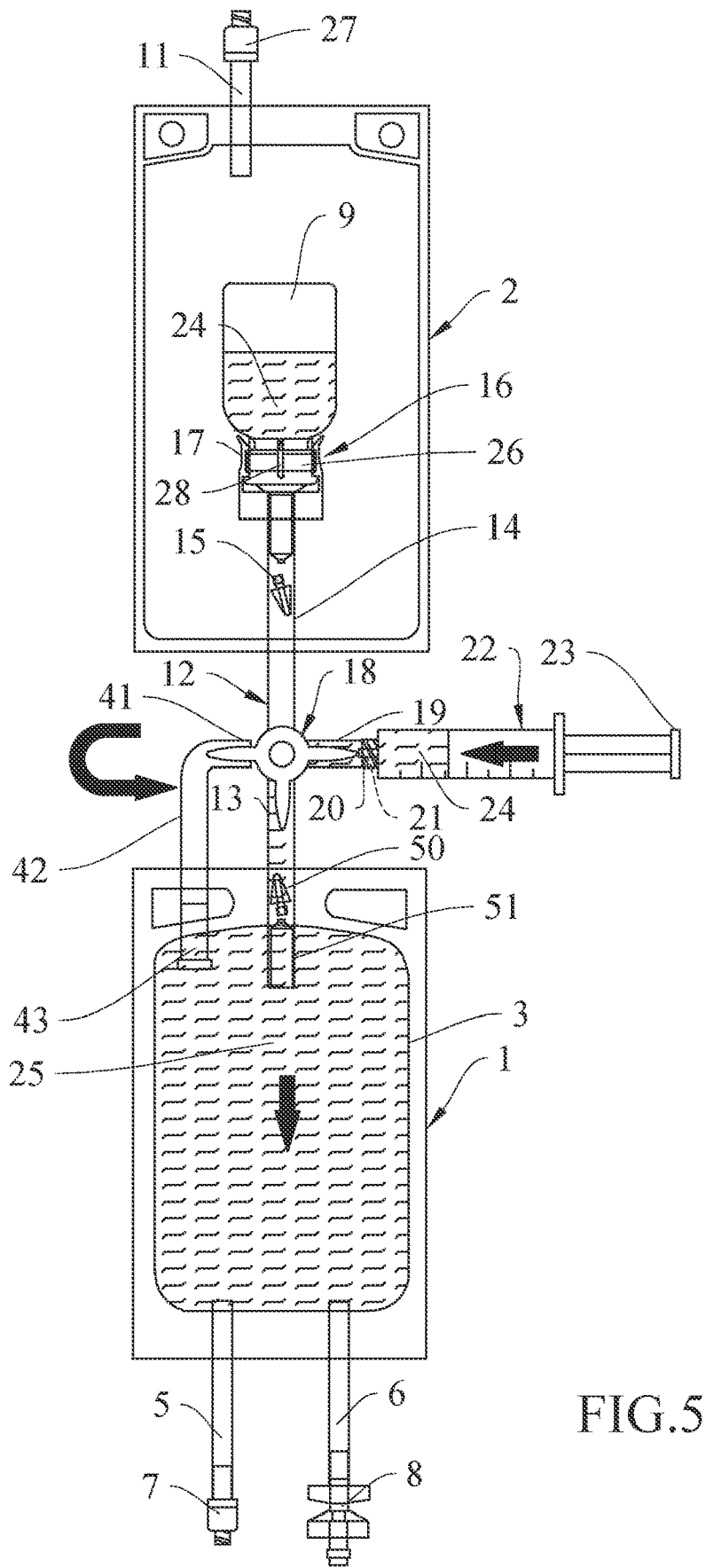

By pulling backwards the plunger 23 as in FIG. 4, the desired quantity of mixture 24 is sucked in the syringe 22, which mixture—once the flow diverter 18 is turned into the position shown in FIG. 5 (same as FIG. 2)—can be delivered into the bag 3 by pushing forwards the plunger 23 and thus creating a drug or nutrient 25 with the desired dosing. Also at this stage, the flexible tube 42 with hydrophobic filter 43 serves as a pressure compensator terminating into a sterile casing.

Figure 6:
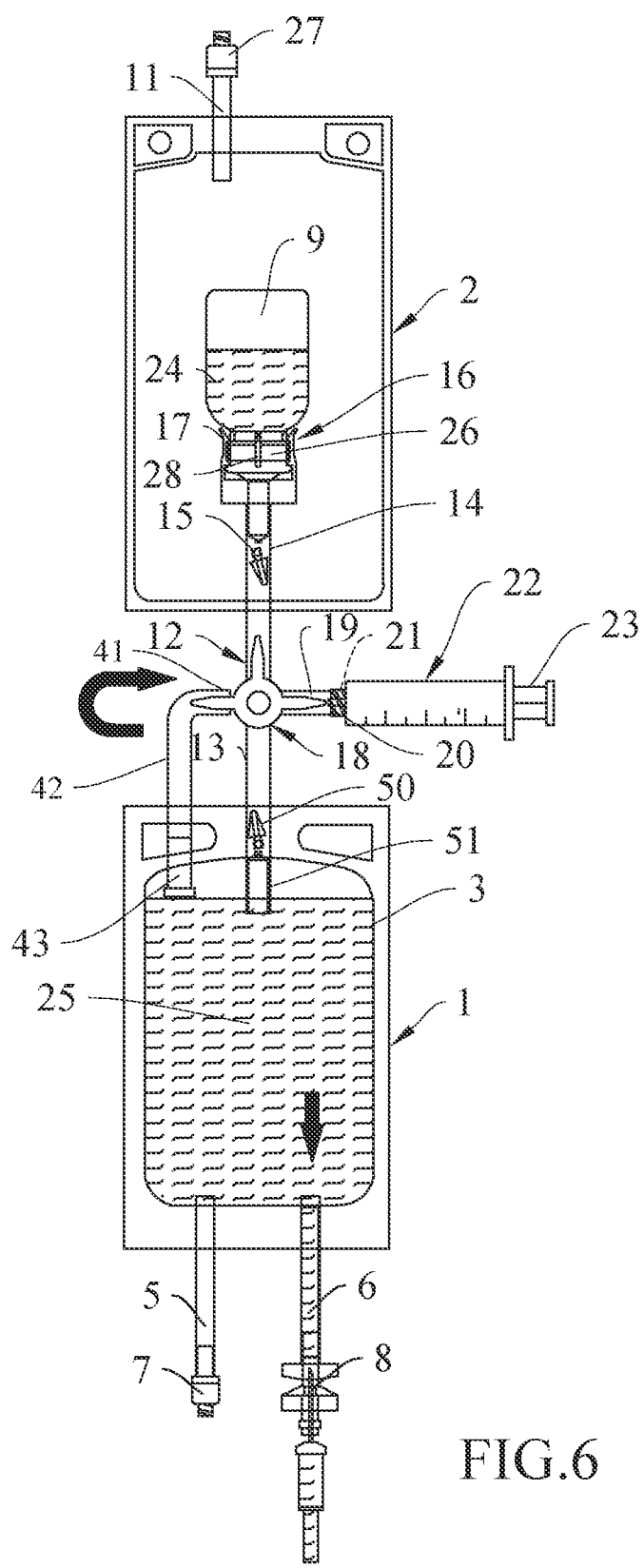
FIG. 6 shows the package once the procedures are completed.
Figure 7:
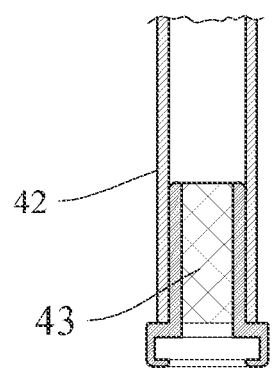
FIG. 7 is a sectional view of one end of the tube with hydrophobic filter serving as a pressure compensator, on a magnified scale.

The flow diverter 18 is eventually adjusted as shown in FIG. 6, while the luer 21 of the syringe 22 is still inside the cap 20.

The process of dosed reconstitution of the drug or nutrient is complete and the cap 8 can be opened (FIG. 6) in order to supply said drug or nutrient to the patient.

What is claimed is:

1. A package comprising:
   a first flexible sterile casing,
   a second flexible sterile casing spatially separated from the first flexible casing by a distance, a tube coupled to the first flexible sterile sealed casing and the second flexible sterile sealed casing, wherein the tube has a middle portion extending between the first and second casings;

an adjustable flow diverter disposed in the middle portion of the tube extending between the first and second casings, the flow diverter comprising a first side opening in fluid communication with the tube and configured to receive a syringe, wherein the flow diverter is configured to be adjusted to a plurality of positions to selectively allow the first side opening to be in fluid communication with the first and second casings, and a pressure compensator comprising a flexible tube with a hydrophobic filter connected to a second side opening of said flow diverter and terminates in the first or second casing.

2. The package according to claim 1, wherein the flow diverter comprises a multi-way stopcock.

3. The package according to claim 1, further comprising:
a sterile bag filled with liquid diluent, and
a bottle equipped with a pierceable cap to contain a medicinal or nutritional substance in powder, or gel,
wherein the tube extends from the bag and ends with a coupling and perforation device disposed at the cap of the bottle, where the bag is housed in the first casing and the bottle and the coupling and perforation device are housed in the second casing,
wherein the coupling and perforation device comprises flaps configured to be coupled to the cap of the bottle and a perforation tip configured to pierce the cap of the bottle after said cap has been coupled to the flaps and pressure has been exerted on an outer wall of the second casing to bring the bottle closer to the bag in an axial direction along the tube.

4. The package according to claim 1, wherein the second casing is equipped with a tube connector to deliver a mixture of sterilizing gas and oxygen into the second casing.

5. The package according to claim 3, wherein between the middle portion of the tube extending between the first and second casings and said coupling and perforation device, said tube includes a final portion housing a frangible closure.

6. The package according to claim 3, wherein the tube includes an initial portion extending from said first casing and terminating into said bag, the initial portion housing a frangible closure.

7. The package according to claim 3, wherein the plurality of positions include:
a first position wherein the flow diverter allows the bag housed in the first casing to be in communication with the first side opening of the flow diverter, and the first side opening includes an openable and hermetically sealable cap for receiving a syringe, and
a second position wherein the flow diverter allows the bottle housed in the second casing to be in communication with the first side opening of the flow diverter.

* * * * *